United States Patent [19]

Lebigot

[11] Patent Number: 4,781,177

[45] Date of Patent: Nov. 1, 1988

[54] BLOOD CLOTS FILTERING DEVICE

[75] Inventor: Jacques Lebigot, Saint-Barthelemy, Guadeloupe

[73] Assignee: Promed, Saint-Barthelemy, Guadeloupe

[21] Appl. No.: 120,995

[22] Filed: Nov. 16, 1987

[30] Foreign Application Priority Data

Nov. 17, 1986 [FR] France ............... 86 15962

[51] Int. Cl.⁴ .......................................... A61B 17/00
[52] U.S. Cl. ................... 128/897; 128/303 R; 128/325; 128/345; 210/446; 210/767
[58] Field of Search .............. 128/1 R, 130, 303 R, 128/325, 345; 210/446, 767

[56] References Cited

U.S. PATENT DOCUMENTS

| | | | |
|---|---|---|---|
| 3,540,431 | 11/1970 | Uddim | 128/1 |
| 3,952,747 | 4/1976 | Kimmell, Jr. | 128/303 R |
| 4,425,908 | 1/1984 | Simon | 128/1 R |
| 4,643,184 | 2/1987 | Mobin-Uddin | 128/303 R |
| 4,688,553 | 8/1987 | Metals | 128/303 R |

Primary Examiner—Edward M. Coven
Assistant Examiner—Randy Citrin
Attorney, Agent, or Firm—Weingarten, Schurgin, Gagnebin & Hayes

[57] ABSTRACT

Filtering device useful for partly interrupting the inferior vena cava and for creating an efficient barrier against embolic migration; in the expanded operating condition, said device comprises a filiform body, extended at one of its ends by a plurality of diverging flexible wires, which wires are regularly circumferentially spaced apart one with respect to the other, while the free end of each one is bent outwardly to form a fastening tip, the other end of said body ending in a stabilizer which also acts as a second filter, constituted of a plurality of flexible wires, diverging around said body, which wires are regularly circumferentially spaced one with respect to the other and are offset of a certain angle with respect to the wires constituting the first filter.

9 Claims, 1 Drawing Sheet

BLOOD CLOTS FILTERING DEVICE

FIELD OF THE INVENTION

The present invention relates to a filtering device useful for causing a partial interruption of the inferior vena cava in the treatment of thrombo-embolic disorders; this filtering device is designed to be introduced in the inferior vena cava of the human body, downstream of the emboligenic center, in order to stop the clots transported by the flow of blood in the inferior vena cava of the lower part of the human body, the object being to bar the way to emboli migration towards the flow of blood through the lungs.

BACKGROUND OF THE INVENTION

Filters have already been proposed for insertion in the vascular system in order to stop the emboli.

U.S. Pat. No. 3,540,431 describes an umbrella-shaped intravascular filter which comprises divergent arms ending with a tip, and a cap of filtering medium.

U.S. Pat. No. 3 952 747 describes another type of intravascular filter comprising a plurality of divergent arms, joined together by one of their ends, each one ending into a hook at their free end, said arms further comprising U-loops.

Said filters are inserted inside the vena cava where they are held in position by the tips or hooks in contact with the vein inner wall. They are not, however, safely balanced, and it may happen that, under the effect of the flowing blood or of the movements of the vein, these filters topple and become detached from the vein inner wall, thereafter migrating dangerously through the vein and even reaching up to the right auricle of the heart, where they can cause incurable perforations.

Moreover, such filters are not reliable in that their relatively wide meshes can allow part of the emboli to escape and that their filtering capacity is limited.

SUMMARY OF THE INVENTION

It is the object of the invention to propose a filtering device which can eliminate the drawbacks of the conventional filters.

The filtering device according to the invention comprises, in its expanded operating condition, a filiform body extended at one of its ends by a first filter constituted by a plurality of flexible wires, of identical length and configuration, starting from said end and diverging in extension from said body, said wires being regularly circumferentially spaced apart one with respect to the other, so as to form a cone of revolution, widened and open at its base, the free end of each wire being bent outwardly to form a fastening tip; the other end of said body ends in a stabilizer which also acts as second filter, and is constituted of a plurality of flexible wires of identical length and configuration, starting from said other end, and which are first bent over around said body and diverging with respect thereto; said wires are regularly circumferentially spaced apart one from the other and are, moreover, offset of a certain angle with respect to the wires constituting the first filter, in order to form a second cone of revolution widened and open at its base; the free end of each wire is slightly bent inwardly to prevent any fastening; an eyelet being also provided at said other end of the body for threading through a silk thread for positioning the filtering device.

In the collapsed condition, for the purpose of being housed inside a catheter, the wires of the filter-stabilizer are resiliently bent against said body and the wires of the first filter are resiliently bent over the axis extending from said body.

More particularly, the first filter is constituted by six flexible wires regularly circumferentially spaced apart of 60° one with respect to the other; the filter-stabilizer is constituted by six flexible wires which are regularly circumferentially spaced of 60°, one with respect to the other, and which are angularly offset of 30° with respect to the wires of the first filter.

In one particular embodiment of the filtering device according to the invention, each one of the wires constituting the first filter is secured to one of the wires constituting the filter-stabilizer by an intermediate piece of wire to form a pin-like element, a certain number of such pin-like elements being juxtaposed and joined together by their intermediate pieces by means of a tubular sleeve in order to make up the first filter, the body and the filter-stabilizer.

The filtering device according to the invention and more particularly the flexible wires which constitute it, can be produced from any elastically-deformable material, conventionally used for producing intravascular filters, and preferably in a medical-grade stainless steel.

DETAILED DESCRIPTION OF THE INVENTION

The invention will be more readily understood on reading the following description with reference to the accompanying drawings, in which.

Figure 1:
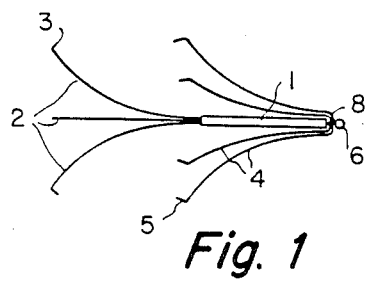
FIG. 1 is a side elevation of the filtering device according to the invention.
Figure 2:
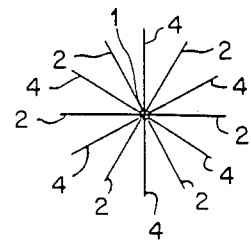
FIG. 2 is a view of the filtering device shown in FIG. 1, seen from the left.

Referring first to FIGS. 1 and 2, these show that the filtering device according to the invention, which is shown in the expanded operating position comprises a body (1), generally filiform and extended at one of its ends by a first filter constituted by a plurality of flexible wires (2) (such as for example, six wires of medical-grade stainless steel) of identical length and configuration, starting from said end and diverging in extension of the body, said wires being moreover regularly circumferentially spaced apart one from the other (for example by 60°) in order to form a cone of revolution widened and open at its base; the free end of each wire is bent outwardly at right angle to form a tip (3) for fastening the wire to the inner wall of the vein.

The other end of the body (1) is ended by a stabilizer acting also as a second filter, constituted of a plurality of wires (4) (such as, for example, six wires in medical grade stainless steel) of identical length and configuration, which start from said second end and are first bent over around said body and progressively diverging from the latter; said wires are regularly and circumferentially spaced one with respect to the other (for example with a 60° spacing) while being angularly offset (for example of 30°) with respect to the wires constituting the first filter, in order to form a second cone of revolution widened and open at its base; the free end (5) of each wire is slightly bent or curved inwardly to prevent it from fastening to the inner wall of the vein.

An eyelet (6) is also provided at said second end of the body (1) to allow the passage of a silk thread for positioning the filtering device according to the invention in the inferior vena cava, by means of catheter as will be explained hereinafter.

Figure 3:
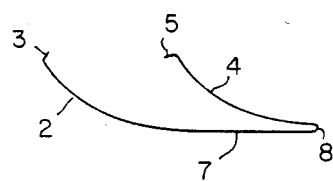
FIG. 3 shows a pin-like element used in the production of said filtering device.

According to one special embodiment of the filtering device, each one of the wires (2) constituting the first filter is joined to one of the wires (4) constituting the filter-stabilizer by an intermediate piece of wire (7) in order to form a pin-like element, as illustrated in FIG. 3; more particularly, taking a flexible wire (7), this is incurved slightly at one of its ends in order to form element (2), the end of which element is bent at right angle outwardly to form the fastening tip (3); the other end of the wire (7) is bent first over itself in parallel to said wire, thus forming a loop (8), then it is bent outwardly to form element (4), which latter is thereafter angularly offset from element (2) of 30° by a slight twisting operation; then the end of element (4) is bent inwardly.

Six pin-like elements, formed as above-described are joined together by their central portions by means of a tubular sleeve (1) to make-up the first filter, the body (1) and the filter-stabilizer; a wire provided with an eyelet (6) is inserted in the center of the pin-like elements before the sleeve is crimped.

By way of example and non-restrictively, the abovedescribed filtering device is produced from a wire made of medical-grade stainless steel with a diameter of 3/10th of a millimeter, and the crimping sleeve, also in stainless steel has a bore of 1 mm diameter with an external diameter of 2 mm; the total length of the filtering device is 6 cm, the length of the body (1) being 2.5–3 cm and the distance between the two filters (measured between the free ends of wires (2) and (4)) is 3.0 to 3.5 cm; the diameter of the cone base being 3 cm and, the radius of curvature of wires (2) and (4) being 3 cm.

The filtering device according to the invention can be inserted by percutaneous route or after surgical access, into the jugular vein at the base of the neck, by means of a radioopaque catheter, and released at the wanted spot.

Figure 4:
FIG. 4 is a view of the filtering device in collapsed condition and housed inside a catheter.

To this effect, the filtering device according to the invention, such as illustrated in FIG. 4 in collapsed condition, is housed in a catheter (9) (for example, of inner diameter 3.2 mm, of outer diameter 4 mm, and of length 60 cm) inside which a canula (10) is placed (for example of 1.2 mm inner diameter, 2.5 mm outer diameter and 70 cm length) which canula is traversed by a silk thread (11) threaded through eyelet (6). A Luer-Lock type assembling system is provided for fastening the canula to the catheter.

Figure 5:
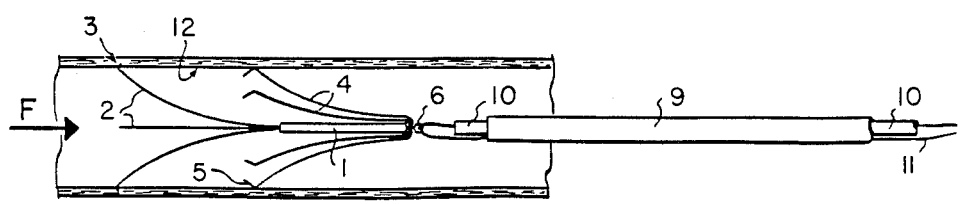
FIG. 5 is a view of the filtering device in expanded condition, positioned in the inferior vena cava.

As illustrated in FIGS. 4 and 5, the silk thread (11) threaded through the eyelet defines two strands of threads the free ends of which project from the catheter. These two strands can traverse the canula, but, advantageously, to prevent them from becoming entangled, one of the two strands traverses the canula (10) while the other traverses the space defined between the canula (10) and the catheter (9).

The catheter (9) is introduced into the internal jugular vein at the base of the neck and is pushed through the superior vena cava and into the inferior vena cava.

As soon as the target spot is reached, the canula (10) is immobilized, and the catheter (9) is gradually withdrawn, thereby releasing the first filter which expands into the vein, its tips (3) fastening to the inner wall of said vein (12). A slight pull is exerted on the silk thread (11) to ensure the fastening. By continuing to withdraw the catheter, the filter-stabilizer is released and expands, and its wires (4) come to rest against the inner wall of the vein.

The whole assembly composed of the catheter (9) and the canula (10) and finally the silk thread (11) are withdrawn.

If the filtering device is inaccurately positioned, it is possible to retrieve it by progressively pushing the catheter (10) so as to insert first the filter-stabilizer, then the first filter into said catheter, and to replace the filtering device in another spot, this operation constituting an advantage of the invention.

The method for positioning the filtering device according to the invention is simple and not really traumatizing for the patient, compared with the surgical interventions required for positioning the conventional filters, and it can be used on patients whose state of health is very precarious. Its insertion by percutaneous route makes it possible to initiate a fibrinolytic treatment without any risk. Its positioning can be controlled by simple X-ray of the abdomen or by scannographic examination.

It is possible with the device according to the invention, thus positioned in the inferior cava vena, to partly interrupt said vein and to create an efficient barrier against emboli migration, with only little repercussion on the blood flow.

The emboli transported by the blood flow through the veins in the direction of arrow (F), are trapped and stopped by the first filter, and those which have been able to escape from said first filter through the wire (2), are stopped by the second filter of which the wires (4) are angularly offset of 30° with respect to wires (2).

In addition to the fact that it doubles the filtering capacity of the filtering device, the filter-stabilizer, because of its configuration into an open-base cone, which gives it good flexibility, is not rigidly blocked against the inner wall of the vein, and can be elastically deformed while following the movements of the vein, keeping in contact with the vein wall, without interfering with the first filter which remains fastened in a stable manner to the vein inner wall, this contributing to the patient's comfort, as well as to making the filtering device safe to use.

What is claimed is:

1. A filtering device useful for partly interrupting the interior vena cava and for creating an efficient barrier against embolic migration, wherein in as expanded operating condition, said device comprises:

a filiform body, extended at one of its ends by a first filter constituted by a plurality of flexible wires of identical length and configuration, starting from said end and diverging in extension from said body, said wires being regularly circumferentially spaced apart, one with respect to the other, so as to form a cone of revolution, widened and open at its base, the free end of each wire being bent outwardly to form a fastening tip;

a filter-stabilizer located at the other end of said body and constituted of a plurality of flexible wires of identical length and configuration, starting from said other end, and which are first bent over around said body and diverging with respect thereto, said wires being regularly circumferentially spaced apart, one from the other, and being, moreover, offset by a certain angle with respect to the wires constituting the first filter, in order to form a second cone of revolution widened and open at its base, the free end of each wire being slightly bent inwardly to prevent any fastening;

and an eyelet being also provided at said other end of the body for threading a thread therethrough for positioning the filtering device;

whereas in the collapsed state, the wires of the filter-stabilizer, in order to be housed in a catheter, are resiliently bent against said body and the wires of the first filter are resiliently bent over the axis extending from said body.

2. The filtering device of claim 1, wherein the first filter is constituted by six flexible wires regularly circumferentially spaced apart by 60°, one with respect to the other, and wherein the filter-stabilizer is constituted by six flexible wires which are regularly circumferentially spaced by 60°, one with respect to the other, and which are angularly offset by 30° with respect to the wires of the first filter.

3. The filtering device of claim 2, wherein each one of the wires constituting the first filter is secured to one of the wires constituting the filter-stabilizer by an intermeidate piece of wire to form a pin-like element, a certain number of such pin-like elements being juxtaposed and joined together by their intermediate pieces by means of a tubular sleeve in order to make up the first filter, the body and the filter-stabilizer.

4. The filter device of claim 1, wherein the flexible wires which constitute the first filter and the filter-stabilizer are made of any elastically-deformable material conventionally used for producing intravascular filters.

5. The filtering device of claim 4, wherein the elastically-deformable material is medical-grade stainless steel.

6. A system comprising:
a filtering device, wherein in an expanded operating condition, said filtering device comprises:
a filiform body, extended at one of its ends by a first filter constituted by a plurality of flexible wires of identical length and configuration, starting from said end and diverging in extension from said body, said wires being regularly circumferentially spaced apart, one with respect to the other, so as to form a cone of revolution, widened and open at its base, the free end of each wire being bent outwardly to form a fastening tip;
a filter-stabilizer located at the other end of said body and constituted of a plurality of flexible wires of identical length and configuration, starting from said other end, and which are first bent over around said body and diverging with respect thereto, said wires being regularly circumferentially spaced apart, one from the other, and being, moreover, offset by a certain angle with respect to the wires constituting the first filter, in order to form a second cone of revolution widened and open at its base, the free end of each wire being slightly bent inwardly to prevent any fastening;
and an eyelet being also provided at said other end of the body for threading a thread therethrough for positioning the filtering device;
whereas in the collapsed state, the wires of the filter-stabilizer, in order to be housing in a catheter, are resiliently bent against said body and the wires of the first filter are resiliently bent over the axis extending from said body;
a catheter for housing said filtering device in collapsed condition;
a canula housed in said catheter;
and a thread which extends through said catheter and passes through said eyelet of said filtering device so as to form two strands, the free ends of which emerge from the catheter, said canula being connectable to the catheter.

7. The system of claim 6, wherein one of said strands in threaded through said canula whereas the other traverses the space defined between said canula and the catheter.

8. A method for causing a partial interruption of the interior vena cava in the treatment of thrombo-embolic disorders, consisting essentially of:
providing a system comprising:
a filtering device, wherein in an expanded operating condition, said filtering device comprises:
a filiform body, extended at one of its ends by a first filter constituted by a plurality of flexible wires of identical length and configuration, starting from said end and diverging in extension from said body, said wires being regularly circumferentially spaced apart, one with respect to the other, so as to form a cone of revolution, widened and open at its base, the free end of each wire being bent outwardly to form a fastening tip;
a filter-stabilizer located at the other end of said body and constituted of a plurality of flexible wires of identical length and configuration, starting from said other end, and which are first bent over around said body and diverging with respect thereto, said wires being regularly circumferentially spaced apart, one from the other, and being, moreover, offset by a certain angle with respect to the wires constituting the first filter, in order to form a second cone of revolution widened and open at its base, the free end of each wire being slightly bent inwardly to prevent any fastening;
and an eyelet being also provided at said other end of the body for threading a thread therethrough for positioning the filtering device;
whereas in the collapsed state the wires of the filter-stabilizer, in order to be housed in a catheter, are resiliently bent against said body and the wires of the first filter are resiliently bent over the axis extending from said body;
introducing the catheter into the jugular vein at the base of the neck;
pushing said catheter through the superior vena cava until it reaches a predetermined spot in the inferior vena cava;
immmobilizing the cannula;
progressively removing the catheter to release the first filter which expands inside the vein inner wall;
exerting a slight pull on the thread to secure the fastening;
and removing the catheter in order to release the filter-stabilizer which expands until its wires are resting against the vein inner wall.

9. The method of claim 8 wherein after releasing said filter-stabilizer, the assembly composed of the catheter and the canula are first removed, and then thread is removed.

* * * * *